(12) United States Patent
Schröder et al.

(10) Patent No.: US 8,765,980 B2
(45) Date of Patent: Jul. 1, 2014

(54) ORGANIC COMPOUNDS

(75) Inventors: Fridtjof Schröder, Hettlingen (CH); Urs Mueller, Kanchanaburi (TH); Peter Gygax, Maur (CH)

(73) Assignee: Givaudan S.A., Vernier (CH)

( * ) Notice: Subject to any disclaimer, the term of this patent is extended or adjusted under 35 U.S.C. 154(b) by 116 days.

(21) Appl. No.: 13/515,842

(22) PCT Filed: Dec. 17, 2010

(86) PCT No.: PCT/EP2010/070070
§ 371 (c)(1),
(2), (4) Date: Jul. 11, 2012

(87) PCT Pub. No.: WO2011/073387
PCT Pub. Date: Jun. 23, 2011

(65) Prior Publication Data
US 2012/0271059 A1    Oct. 25, 2012

(30) Foreign Application Priority Data
Dec. 18, 2009 (GB) .................. 0922204.3

(51) Int. Cl.
C07C 67/32 (2006.01)
C07D 307/92 (2006.01)

(52) U.S. Cl.
CPC .................... C07C 67/32 (2013.01)
USPC .................... 549/458; 560/128

(58) Field of Classification Search
CPC .................... C07C 67/32
USPC .................... 549/458; 560/128
See application file for complete search history.

(56) References Cited

U.S. PATENT DOCUMENTS

2008/0064886 A1    3/2008    Frater et al.

FOREIGN PATENT DOCUMENTS

WO    WO 2007/098791    8/2007
WO    WO 2008/010287    2/2008

OTHER PUBLICATIONS

PCT/EP2010/070070—International Search Report, Mar. 11, 2011.
PCT/EP2010/070070—International Written Opinion, Mar. 11, 2011.
PCT/EP2010/070070—International Preliminary Report on Patentability, Jun. 19, 2012.
GB0922204.3—Great Britain Search Report, May 19, 2010.
Kolsaker P., et al.: "On the Reaction of the Half Ester of 2-Methylpropylidene Malonic Acid with N-Bromosuccinimide. Preparation of Ethyl Methyl (E)-2-Bromo-2-methylpropylidenemalonate", Acta Chemica Scandanavia, vol. 35, pp. 701-705, Jan. 1, 1981.
Wentrup, Curt, et al.; "Mechanism of Fragmentation of Alkylidene-Meldrum's Acids. Carboxyketene, Vinylketene, and Methyleneketene Intermediates from 5-Cyclopentylidene-2,2-dimethyl-1, 3-dioxane-4,6-dione", Journal of Organic Chemistry, vol. 50, pp. 2877-2881, Aug. 1, 1985.
Krapcho A.P.: "Synthetic Applications of Dealkoxycarbonylations of Malonate Esters, Beta-Keto Esters, Alpha-Cyano Esters and Related Compounds in Dipolar Aprotic Media—Part 1", Synthesis, pp. 805-822, Oct. 1, 1982.
Schulte-Elte, et al.: "An Alternative Access to (±)-α -Irones and (±)-β-Irone via Acid-Mediated Cyclisation", Helvetica Chemica Acta, vol. 75, pp. 759-765, 1992.
Krapcho A.P.: °Synthetic Applications and Mechanism Studies of the Decarbalkoxylations of Geminal Diesters and Related Systems Effected in Me2S0 by Water and/or by Water with Added Salts , Journal of Organic Chemistry, vol. 43, pp. 138-147,1978.
Krapcho A.P.: "Synthetic Application of Dealkoxycarbonylations of Malonate Esters, β-Keto Esters, α-Cyano Esters and Related Compounds in Dipolar Aprotic Media—Part II", Synthesis, pp. 893-914, Oct. 1, 1982.

*Primary Examiner* — Taofiq A Solola
(74) *Attorney, Agent, or Firm* — Curatolo Sidoti Co., LPA; Joseph G. Curatolo; Salvatore A. Sidoti

(57) ABSTRACT

A process for the preparation of β,γ-unsaturated-γ, γ-disubstituted esters 1 with high E/Z- and β,γ/α,β-ratios, Formula (1) by reacting at a temperature of between about 130 and 170 degrees centigrade the conjugated malonate Formula (3) with, a group I, II or III metal halide or an organic cation/halide anion pair, an inorganic proton source and a polar solvent.

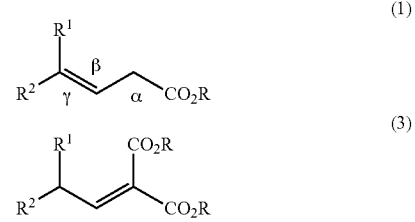

14 Claims, No Drawings

ORGANIC COMPOUNDS

CROSS REFERENCE TO RELATED APPLICATIONS

This application is a national stage application of International Application No. PCT/EP2010/070070, filed 17 Dec. 2010, which claims priority from Great Britain Patent Application No. 0922204.3, filed 18 Dec. 2009, from which applications priority is claimed, and which are incorporated herein by reference.

The present invention is concerned with β,γ-unsaturated-γ,γ-disubstituted esters and with methods of synthesizing same.

β,γ-unsaturated-γ,γ-disubstituted esters 1 can be prepared by various methods known in the art.

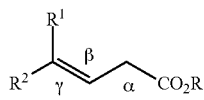

Such methods include (a) isomerization of α,β-unsaturated esters, (b) selective reduction of α,β,γ,δ-unsaturated esters, (c) cyanation of allylic halides, followed by hydrolysis and esterification, (d) carbonylation of allylic halides or (activated) allylic alcohols in the presence of Pd- or Ru-catalysts and (e) by other methods such as cross metathesis.

High E/Z-ratios of 1, however, are usually not obtained through these methods, unless stereopure E-allylic alcohols or halides are used as precursors (in case of c or d), whose synthesis is difficult.

WO 2007096791 describes the transesterification/decarboxylation of conjugated malonate 3a for the E-selective synthesis of 1a, using a salt $MX_n$ (with n=1-3, X being a halide or an anion of an acid HX and M being a group I, II or III metal) in the presence of a carboxylic acid of the type $R'CO_2H$ with R' representing a hydrocarbon group.

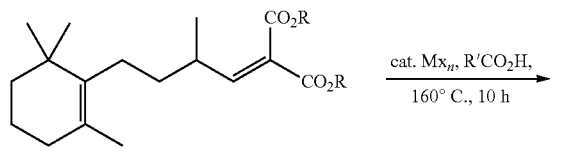

3a

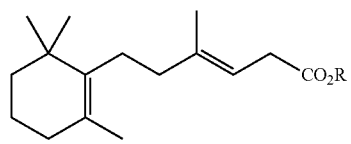

1a

Although high E/Z-ratios and β,γ/α,β ratios were reported from this method, these results were only obtained with substoichiometric amounts of the relatively expensive calcium 2-ethylhexanoate in combination with stoichiometric amounts of 2-ethylhexanoic acid, which after transesterification to allyl 2-ethylhexanoate has to be separated from product 1a. Other $MX_3/R'CO_2H$ combinations claimed in this patent are less efficient.

There remains a need to provide synthetic procedures into β,γ-unsaturated-γ,γ-disubstituted esters, which procedures are carried out relatively inexpensively and which provide 1 with high purity, in particular with high E/Z Ratios.

The invention provides in one of its aspects a process for the preparation of β,γ-unsaturated-γ,γ-disubstituted esters 1,

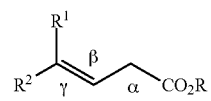

said process comprising the step of reacting at a temperature of between about 100 to about 350, more particularly about 130 to about 170 degrees centigrade the conjugated malonate

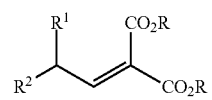

with a $MX_n$, in the presence of an inorganic proton source and optionally a polar solvent, wherein $MX_n$ is an inorganic salt or an organic cation/halide anion pair, X is a halide and n is an integer of 1 to 3, and M is a group I, II or III metal when $MX_n$ is an inorganic salt, or M is selected from the group consisting of pyrridinium, piperidinium, pyrrolidinium, imidazolium, ammonium, phosphonium and sulphonium, when $MX_n$ is an organic cation/halide anion pair; and wherein the groups $R^1$, $R^2$ and R are organic residues.

The skilled person will appreciate that the compound 1 is an interesting intermediate, which may be employed in synthetic mutes to many interesting end products in the chemical arts and the nature of the $R^1$, $R^2$ and R will depend on the desired end product. In particular, the substituents $R^1$, $R^2$ and R can be chosen from substituents useful in the fragrance art. More particularly, the substituents may be independently selected from hydrogen; linear, branched or (poly)cyclic $C_{1-15}$ alkyl, aryl or arylalkyl groups, which optionally contain unsaturated bonds and/or 1 to 4 heteroatoms independently selected from O, S, N and Si. The groups R on the malonate 3 can be the same or different or together can form a (poly) cyclic group, optionally containing unsaturation or substituents as hereinabove defined.

Particularly preferred substituents R include methyl and ethyl.

Particularly preferred substituents $R^1$ include methyl, phenyl, 2-(2,6,6-trimethylcyclohex-1-enyl)-ethyl, 4,8-dimethyl-nona-3,7-dien-1-yl.

Particularly preferred substituents $R^2$ include methyl, phenyl, 2-(2,6,6-trimethylcyclohex-1-enyl)-ethyl, 4,8-dimethyl-nona-3,7-dien-1-yl.

Compound 1 formed by a process of the present invention can exist as an isomer mixture, with the double bond located in the β,γ-position or in the α,β-position, and if $R^1 \neq R^2$ in the β,γ-isomer, E/Z isomers are possible. The present invention provides a process for the preparation of 1 with high β,γ/α,β ratio, in particular of at least 95:5. The compounds 1 can also be formed with high E/Z-ratio, in particular of at least 75:25, more particularly at least 80:20.

Compounds 1 formed by a process of the present invention are useful compounds and may be used as reagents in all manner of organic syntheses.

Examples of 1 are cyclohomofarnesic ester 1a and homofarnesic ester 1b, whose E-isomers are valuable precursors for the synthesis of (3aR,5aS,9aS,9bR)-3a,6,6,9a-tetramethyl-dodecahydro-naphtho[2,1-b]furan 2 (Ambrox), which can be prepared from 1a or 1b for example as described in WO 2006010287 (Givaudan). The stereochemical descriptors 3aR,5aS,9aS,9bR refer to the relative as well as to the absolute configuration, which means that 2 can be prepared as racemate or enantiomerically enriched, as desired.

Ambrox 2 is an important fragrance ingredient whose olfactory profile is, apart from its enantiopurity, determined by its diastereopurity, which in turn depends on the E/Z-ratios of the cyclization precursors, e.g. the compounds 1a and 1b. Processes are desired, which provide these precursors with high E/Z-selectivity.

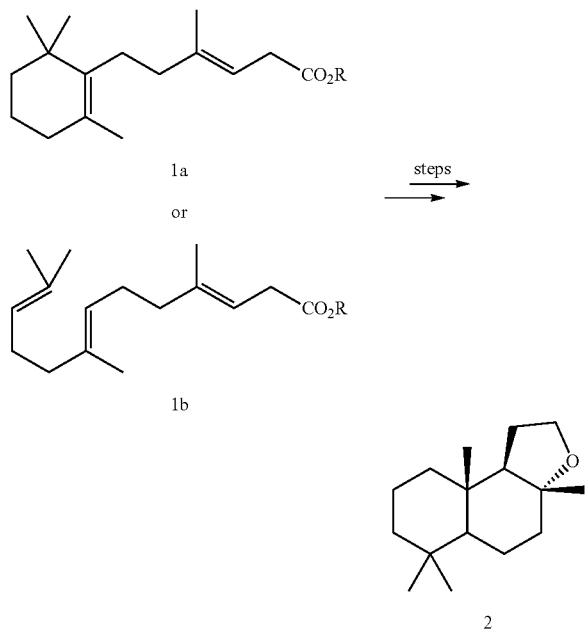

Accordingly, in another aspect of the present invention there is provided a process of preparing (3aR,5aS,9aS,9bR)-3a,6,6,9a-tetramethyl-dodecahydro-naphtho[2,1-b]furan, said process comprising the step of reacting at a temperature of between about 100 to about 350, more particularly about 130 to about 170 degrees centigrade the conjugated malonate 3

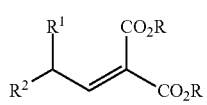

with a $MX_n$ in the presence of an inorganic proton source and optionally a polar solvent, wherein $MX_n$ is an inorganic salt or an organic cation/halide anion pair, X is a halide and n is an integer of 1 to 3, and M is a group I, II or III metal when $MX_n$ is an inorganic salt, or M is selected from the group consisting of pyrridinium, piperidinium, pyrrolidinium, imidazolium, ammonium, phosphonium and sulphonium, when $MX_n$ is an organic cation/halide anion pair; and wherein the group $R^1$ is 2-(2,6,6-trimethylcyclohex-1-enyl)-ethyl or 4,8-dimethyl-nona-3,7-dien-1-yl, $R^2$ is methyl and R is selected from the groups as hereinabove defined.

In yet another aspect of the present invention there is provided (3aR,5aS,9aS,9bR)-3a,6,6,9a-tetramethyl-dodecahydro-naphtho[2,1-b]furan obtainable by a process as hereinabove described.

In yet another aspect of the present invention there is provided a perfume composition comprising (3aR,5aS,9aS,9bR)-3a,6,6,9a-tetramethyl-dodecahydro-naphtho[2,1-b]furan obtainable by a process as hereinabove described.

In yet another aspect of the invention there is provided a consumer product comprising (3aR,5aS,9aS,9bR)-3a,6,6,9a-tetramethyl-dodecahydro-naphtho[2,1-b]furan obtainable by a process as hereinabove described.

The $MX_n$ inorganic salt may be, in particular a group Ia, IIa or IIIb halide, including lanthanide halides such as $CeCl_3$. Preferred inorganic salts are magnesium chloride and lithium chloride.

The $MX_n$ organic cation/halide anion pair may be any of those materials referred to hereinabove. Optionally, the organic cations are substituted with 1-4 alkyl and/or aryl groups, which themselves can be substituted by any functional group. The organic cations can be linked among each other, thus forming a solid phase.

Salt mixtures of low melting points, which are liquid between about 100° C. and 200° C. can be used in the presence or absence of a polar solvent.

The salts may be used singularly or as mixtures.

The amount of salt employed may be 0.2 mol % to 200 mol %, more particularly 1 mol % to 20mol %.

The inorganic proton source can be any inorganic proton donor with a $pK_A$ between about 0 and about 17. Suitable inorganic proton sources include water ($pK_A$ 15.6) or boric acid ($pK_A$ 9.2), which are soluble or partially soluble in the polar solvent. Mixtures of inorganic proton donors such as water/boric acid mixtures may be employed. Other mixtures include boric acid/metaboric acid mixtures. Examples of boric acid proton donors include metaboric acid ($HBO_2$), monoalkyl or monoaryl boric esters ($ROB(OH)_2$ with R=alkyl, aryl and substituted analogs thereof; bisalkyl or bisaryl boric esters ($HOB(OR)_2$ with R=alkyl, aryl and substituted analogs thereof; as well as alkylidene, arylidene or arylalkylidene bridged borates, whose bridges can carry any kind of substituent, including linkers to other borate units.

The amount of inorganic proton source employed will depend upon the nature of the source and how many protons it can provide. In particular, the amount of proton source employed is in the range of about 0.25 to about 2.5 mol equiv, more particularly about 0.5 to about 1.5 equiv. At least 1 mol equivalent of protons will be required to affect transesterification or hydrolysis. In the case of boric acid, 3 protons can be delivered per entity $H_3BO_3$, this proton source could be employed at about 0.35 mol equiv, more preferably about 0.5 mol equiv.

The polar solvent may be any suitable solvent that can dissolve completely or partially the conjugated malonate starting material, the inorganic proton source and the $MX_n$ salt. In particular, polar solvents employed in the present invention are solvents which are partially or completely miscible with water. The polar solvents may be polar aprotic solvents. Polar solvents, which may be mentioned include alcohols, alkyl sulfoxides, sulfolanes, substituted amides, N-substituted pyrrolidones, N-substituted caprolactams and N-substituted ureas. Water-insoluble N-substituted pyrrolidones carrying substituents with more than 4 carbon atoms are included in this invention, as well as organic cation/halide anion pairs, which form ionic liquids at the reaction temperature, which are polar but often not miscible with water.

Included are also mixtures of molten salts, which are liquid between about 100° C. and 200° C. Mixtures of all these solvents can be used.

Whereas alkylsulfoxides and sulfolanes can be employed, it is preferable not to use these materials when compound 1 is to be employed in a synthesis of a fragrance material because of their rather strong and unpleasant odour, which can be rather difficult to remove.

N-substituted pyrrolidones such as N-Methyl-pyrrolidone (NMP) or N-ethyl-pyrrolidone (NEP) are preferred polar aprotic solvents.

The polar solvent can be also used in low amounts, preferably with 1-2 weight equivalents (w/w) based on the amount of conjugated malonate 3. In case of the N-substituted pyrrolidones such as NMP or NEP the solvent can be separated from the salt/water phase after aqueous work-up and is recycled or discarded as such.

The process of the present invention has the advantage that relatively inexpensive reagent combinations, e.g. $MgCl_2$/boric acid, LiCl/boric acid, $MgCl_2$/water or LiCl/water can be used in low amounts, which remain after aqueous work-up of the reaction in the water phase.

A particular preparation of the β,γ-unsaturated-γ,γ-disubstituted esters by the decarboxylation of the conjugated malonate 3 is described in more detail herein below, wherein R=Me or Et. However, the conditions described below apply to the process of the present invention as a generality.

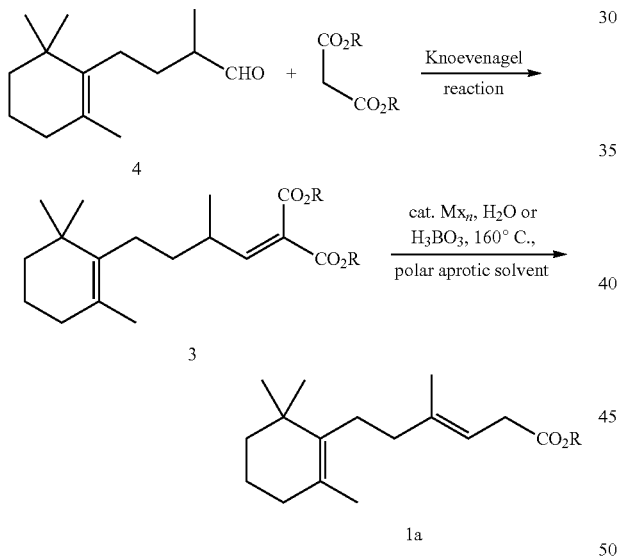

The conjugated malonate starting material may be obtained from commonly available starting materials using routine syntheses. A suitably substituted aldehyde (by way of example, aldehyde 4 shown above) may be reacted with a bisalkyl malonate under Knoevenagel conditions, for which a variety of methods and reagents are known in the art, to provide the conjugated malonate 3, the starting material in a process according to the present invention.

It is preferred to employ as a proton donor one or more of the boric acid proton donors referred to hereinabove (e.g. boric acid) either alone or in admixture with other proton donors.

Water may be employed as the proton donor, but this is not preferred. If the decarboxylation of conjugated malonate 3 to β,γ-ester 1a is to be carried out in the presence of water (or any source of nucleophilic OH⁻) a retro-Knoevenagel-reaction of 3 to aldehyde 4 can occur as a side-reaction. This is disadvantageous as the aldehyde 4 would have to be removed from the desired material 1a.

Reagent systems employing water as the proton donor have been developed that reduce this side reaction particular examples of which include LiCl, $MgCl_2$ or $CaCl_2$ in polar aprotic solvents such as NMP, DMF, DMAA, NEP or in ionic liquids such as [BMIM]Br (see examples). Such reagent systems can reduce the side reaction to a large extent, in particular limiting it to 5 to 10%. These combinations give ester 1a with E/Z-ratios between of 80:20 or more; and good β,γ/α,β ratios, for example 96:4 to 99:1.

With some other water-containing systems the back-reaction to aldehyde 4 may be substantially completely suppressed. In water-containing systems, it is preferred to use N-substituted pyrrolidones such as NOP or NCP with, for example, LiCl or NaCl at 130 to 160 degrees centigrade. 1a can be thus obtained with good E/Z-ratios, for example up to 83:17 and good β,γ/α,βratios. After aqueous work-up the polar solvent such as NOP or NCP remains in the organic phase.

Particularly good E/Z ratios, in particular up to 86:14 may be obtained with boric acid as a transesterification reagent. Boric acid may be used in combination with (earth)alkali halide catalysts such as LiCl, $MgCl_2$ or $CaCl_2$. The solvent may be an N-substituted pyrrolidone such as NMP. Group III metal halides such as $ScCl_3$ or $CeCl_3$ can catalyze this reaction with similar efficiency. Ionic liquid catalysts such as [EMIM]Cl are also effective. Using these catalysts under water-free conditions can avoid formation of byproduct 4.

The invention is further described with reference to the following non-limiting examples.

EXAMPLE 1

Dimethyl 2-(2-methyl-4-(2,6,6-trimethylcyclohex-1-enyl)butylidene)malonate 3a

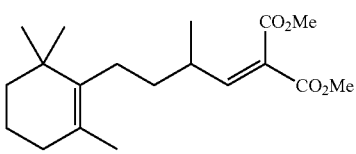 [SMILES: COC(=O)C(=CC(C)CCC1=C(C)CCCC1(C)C)C(=O)OC]

Under water-free conditions titanium(IV) chloride (91 g, 0.5 mol) in tetrachloromethane (120 ml) are added dropwise within 45 min to tetrahydrofuran at 0° C. The mixture is stirred for another 30 min at this temperature, then 2-Methyl-4-(2,6,6-trimethylcyclohex-1-enyl)butanal 4 (50 g, 0.24 mol) (M. Matsui et al., *Agric. Biol. Chem.* 50, 1475-1480, 1986) and dimethyl malonate (31.7 g, 0.24 mol) in tetrahydrofuran (50 ml) are added within 15 min at 0° C. followed by dropwise addition of pyridine (76 g) in tetrahydrofuran (240 ml) over 90 min at 0° C. The orange-brown suspension is stirred for 18 h at 25° C., then poured upon ice/water and extracted with tert-butyl methyl ether. The combined organic layers are washed with water and conc. NaCl and dried over $MgSO_4$. After filtration and evaporation of the solvents the crude product (75 g) is short-path-distilled giving 62.5 g (81%) of 3a at 170° C./0.07 mbar. Analytical data: ¹H NMR (400 MHz, $CDCl_3$): δ 0.95 (s, 6 H), 1.1 (d, 3 H), 1.4-1.5 (4 H), 1.5-1.6 (2 H), 1.58 (s, 3 H), 1.8-2.0 (2 H), 2.5 (m, 1 H), 3.8 (s, 3 H), 3.85 (s, 3 H), 6.85 (d, 1 H) ppm. ¹³C-NMR (400 MHz, $CDCl_3$): δ 19.45 (t), 19.55 (q), 19.75 (q), 26.4 (t), 28.5 (q), 32.7 (t), 34.8

(s), 35.7 (d), 36.8 (t), 39.7 (t), 52.1 (q), 52.2 (q), 126.7 (s), 127.1 (s), 136.8 (s), 154.9 (d), 164.4 (s), 166.0 (s). MS (EI): m/z (%) 322 (M+, 10), 307 ([M-15]+, 2), 275 (6), 259 (7), 243 (16), 215 (11), 200 (18), 187 (19), 175 (20), 173 (16), 172 (100), 153 (22), 145 (28), 140 (70), 137 (27), 135 (34), 123 (60), 122 (28), 121 (42), 109 (35), 108 (34), 95 (62), 93 (36), 81 (44), 79 (33), 55 (36), 41 (35). IR (film): 2950 (m), 2926 (m), 2865 (m), 1725 (s), 1642 (w), 1454 (w), 1433 (m), 1363 (w), 1327 (w), 1246 (s), 1221 (s), 1204 (s), 1168 (w), 1104 (w), 1054 (m), 991 (w), 945 (w), 925 (w), 833 (w), 762 (w).

EXAMPLE 2

Diethyl 2-(2-methyl-4-(2,6,6-trimethylcyclohex-1-enyl)butylidene)malonate 3b

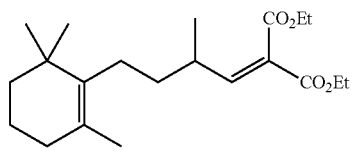 [SMILES: CCOC(=O)C(=CC(C)CCC1=C(C)CCCC1(C)C)C(=O)OCC]

Under the conditions described in example 1, titanium(IV) chloride (91 g, 0.5 mol), 2-methyl-4-(2,6,6-trimethylcyclohex-1-enyl)butanal 4 (50 g, 0.24 mol) and diethyl malonate (39.7 g, 0.24 mol) in tetrahydrofuran and tetrachloromethane are reacted which each other to give after work-up and short-path-distillation 70.1 g (83%) of 3b. Analytical data: $^1$H-NMR (400 MHz, CDCl$_3$): δ 0.97 (s, 6 H), 1.1 (d, 3 H), 1.25-1.6 (6 H), 1.3 (2t, 6 H), 1.58 (s, 3 H), 1.8-2.0 (2 H), 2.55 (m, 1 H), 4.15-4.35 (2q, 4 H), 6.8 (d, 1 H) ppm. $^{13}$C-NMR (400 MHz, CDCl$_3$): δ 14.0 (q), 14.15 (q), 19.5 (t), 19.6 (q), 19.8 (q), 26.5 (t), 28.5 (q), 32.7 (t), 34.85 (s), 35.6 (d), 36.9 (t), 39.8 (t), 61.1 (t), 61.15 (t), 127.0 (s), 127.5 (s), 136.9 (s), 153.9 (d), 164.0 (s), 165.7 (s). MS (EI): m/z (%) 350 (M+, 4), 335 ([M-15]+, 3), 305 (4), 289 (5), 259 (9), 243 (11), 215 (8), 200 (98), 190 (18), 187 (11), 175 (16), 173 (27), 167 (18), 154 (100), 135 (30), 123 (42), 122 (30), 121 (39), 109 (19), 108 (60), 107 (32), 105 (19), 95 (52), 93 (34), 91 (25), 81 (40), 79 (30), 77 (15), 69 (21), 67 (26), 55 (36), 41 (32), 29 (28). JR (film): 2950 (m), 2960 (m), 2930 (m), 2862 (m), 1725 (s), 1645 (w), 1455 (m), 1375 (m), 1325 (w), 1250 (s), 1222 (s), 1205 (s), 1180 (m), 1170 (m), 1100 (m), 1050 (m), 1030 (m), 950 (w), 865 (w), 800 (w), 765 (w).

EXAMPLE 3

(E)-methyl 4-methyl-6-(2,6,6-trimethylcyclohex-1-enyl)hex-3-enoate 1a-Me (1a with R=Me)

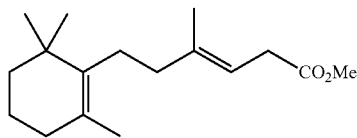 [SMILES: COC(=O)C/C=C(\C)CCC1=C(C)CCCC1(C)C]

Conjugated malonate 3a (0.5 g, 1.5 mmol), anhydrous lithium chloride (93 mg, 2.2 mmol) and water (53 mg, 3 mmol) in N-methyl-pyrrolidone (2.9 g, 29 mmol) are heated under stirring to 130° C. After 4 h at this temperature the mixture is poured upon 2 M HCl and extracted with tert-butyl methyl ether. The combined organic layers are washed with conc. NaHCO$_3$, conc. NaCl and dried over MgSO$_4$. After filtration and evaporation of the solvent the crude product (0.64 g) is bulb-to-bulb-distilled to give 0.4 g of 1a-Me at 120° C./0.1 mbar. E/Z ratio 82:18. Retention times (GC): 9.47 (Z), 9.56 (α,β), 9.62 (E) min. Analytical data of the E-isomer: $^1$H-NMR (400 MHz, CDCl$_3$): δ 1.0 (s, 6 H), 1.4 (m, 2 H), 1.55 (m, 2 H), 1.6 (s, 3 H), 1.7 (s, 3 H), 1.9 (m, 2 H), 2.1 (4 H), 3.05 (d, 2 H), 3.7 (s, 3 H), 5.35 (t, 1 H) ppm. $^{13}$C-NMR (400 MHz, CDCl$_3$): δ 16.35 (t), 19.5 (t), 19.8 (q), 27.5 (t), 28.6 (q, 2C), 32.8 (t), 33.5 (t), 34.95 (s), 39.8 (t), 40.0 (t), 51.6 (q), 115.0 (d), 127.1 (s), 136.9 (s), 139.9 (s), 172.9 (s). MS (EI): m/z (%) 264 (M+, 4), 249 ([M-15]+, 1), 190 (3), 175 (3), 138 (10), 137 (100), 136 (21), 121 (12), 106 (11), 95 (73), 81 (45), 55 (19), 41 (21). The mass spectra of the E- and Z-isomers are identical. IR (film): 2972 (m), 2865 (m), 1738 (s), 1434 (m), 1258 (m), 1199 (m), 1148 (m).

TABLE 1

Variation of some reaction parameters of example 3:

| run | 3 R = | equiv[c] MX$_n$ | equiv[c] H$_2$O | solvent[a] w/w | T [° C.] | t [h] | subst[b] 3a | ald[b] 4 | prod[b] 1a | E/Z | β, γ/α, β |
|---|---|---|---|---|---|---|---|---|---|---|---|
| 1 | Me | 1.5 LiCl | 2 | 6 NMP | 130 | 4 h | | 11% | 79% | 82:18 | 99:1 |
| 2 | Me | 1.5 LiCl | 2 | 13 [BMIM]Br | 130 | 3 h | 11% | 9% | 73% | 71:29 | 96:4 |
| 3 | Me | 1.5 LiCl | 2 | 4 DMF | 130 | 4 h | 4% | 11% | 78% | 81:19 | 96:4 |
| 4 | Me | 1.5 LiCl | 2 | 7 NEP | 130 | 3 h | | 10% | 90% | 80:20 | 99:1 |
| 5 | Me | 1.5 LiCl | 2 | 5 DMAA | 130 | 3 h | | 8% | 90% | 78:22 | 99:1 |
| 6 | Me | 1 CaCl$_2$ | 2 | 10 NMP | 130 | 3 h | | 6% | 92% | 78:22 | 98:2 |
| 7 | Me | 1 CaCl$_2$ | 2 | 6 DMAA | 130 | 3 h | | 10% | 90% | 79:21 | 97:3 |
| 9 | Et | 0.1 MgCl$_2$ | 0.7 + 0.3[e] | 2 NMP | 160 | 6 h | | 6% | 93%[d] | 81:19 | 97:3 |

Decarboxylation of conjugated malonate 3:

[a]w/w = weight equiv. NMP = N-methyl-pyrrolidone, [BMIM]Br = 1-butyl-3-methyl-imidazolium bromide, DMF = dimethyl formamide, NEP = N-ethyl-pyrrolodone, DMAA = dimethyl acetamide.

[b]GC-conversions: Subst = substrate, ald = aldehyde, prod = product.

[c]equiv = molar equivalents.

[d]The product is the ethylester of 1a.

[e]Reaction started with 0.7 equiv water, 0.3 equiv water added after 70% conversion.

TABLE 2

Variation of some reaction parameters of example 3 (giving no back-reaction to aldehyde 4):

| run | 3 R = | equiv[c] MX | equiv[c] H$_2$O | solvent[a] w/w | T [° C.] | time [h] | product[b] 1a | E/Z ratio | β, γ/α, β ratio |
|---|---|---|---|---|---|---|---|---|---|
| 1 | Me | 1.5 LiCl | 2 | 10 NCP | 130 | 2 h | 95% | 83:17 | 99:1 |
| 2 | Me | 1.5 LiCl | 2 | 12 NOP | 130 | 2 h | 90% | 83:17 | 99:1 |
| 3 | Me | 1.5 NaCl | 2 | 10 NCP | 150 | 5 h | 99% | 82:18 | 93:7 |
| 4 | Et | 0.1 LiCl | 0.75 | 2 NMP | 160 | 5 h | 99% | 77:23 | 86:14 |

Decarboxylation of conjugated malonate 3:
[a]w/w = weight equivalents. NCP = N-cyclohexyl-pyrrolidone, NOP = N-octyl-pyrrolidone.
[b]GC-conversions.
[c]equiv = molar equivalents.
d) The product is the ethylester of 1a.

EXAMPLE 4

Preparation of (E)-ethyl 4-methyl-6-(2,6,6-trimethyl-cyclohex-1-enyl)hex-3-enoate 1a-Et (ethyl ester of 1a) by LiCl-catalyzed decarboxylation

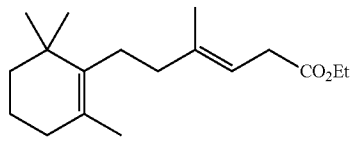 [SMILES: CCOC(=O)C/C=C(\C)CCC1=C(C)CCCC1(C)C]

Under stirring and nitrogen conjugated diethyl malonate 3b (500 g, 1.39 mol), anhydrous lithium chloride (5.6 g, 0.13 mol) and anhydrous boric acid 41 g, 0.65 mol) in water-free N-methyl-pyrrolidone (880 ml, 8.9 mol) are heated to 160-170° C. for 10 h. After cooling the mixture is poured upon 2M HCl. After phase separation the organic phase is washed with conc. NaHCO$_3$ and conc. NaCl. The combined water phases are extracted with toluene. The combined organic layers are evaporated under reduced pressure to give 412 g of crude residue. Short-path-distillation at 150° C./0.06 mbar gives 352 g (91%) of ester 1a-Et. E/Z-ratio: 86:14. The analytical data of this compound are identical with the ones described for the isomers by M. Matsui et al. *Agric. Biol. Chem.* 50, 1475-1480, 1986.

EXAMPLE 5

Preparation of 1a-Et by MgCl$_2$-catalyzed Decarboxylation

Under stirring and nitrogen conjugated diethyl malonate 3b (52 g, 149 mmol), anhydrous magnesium chloride (0.56 g, 5.93 mmol) and anhydrous boric acid (4.5 g, 73 mmol) in water-free N-methyl-pyrrolidone (67 ml, 0.81 mol) are heated to 160-170° C. for 3 h. After cooling to 120° C. water is added and the mixture is acidified to pH 3 with 2 M H$_2$SO$_4$. After extraction with hexane the combined organic layers are washed with water, conc. Na$_2$CO$_3$, 10% HOAc, water and conc. NaCl. The organic phase is dried over MgSO$_4$, filtered and evaporated under reduced pressure giving 42 g of a crude residue, which is bulb-to-bulb-distilled to give 36.6 g (88%) of 1a-Et. E/Z-ratio: 84:16. The analytical data of this compound are identical with the ones described for the isomers by M. Matsui et al. *Agric. Biol. Chem.* 50, 1475-1480, 1986.

TABLE 3

Variation of some reaction parameters of examples 4 and 5:

| run | equiv[f] MX$_n$ | equiv[f] H$_3$BO$_3$ | NMP w/w[a] | T [h] | subst[b] 3b | product[b] 1a-Et | E/Z ratio | β, γ/α, β ratio | Yield[d] |
|---|---|---|---|---|---|---|---|---|---|
| 1 | 0.1 LiCl | 0.5 | 1.8 | 6 h | | 99% | 86:14 | 98:2 | 96% |
| 2 | 1.5 LiCl | 2 | 1.8 | 4 h | | 99% | 82:18 | 98:2 | 90% |
| 3[h] | 2 CaCl$_2$ | 2 | 4 | 2 h | 3% | 84% | 82:18 | 98:2 | 79% |
| 3 | 1.5 LiBr | 2 | 6 | 4 h | | 99% | 82:18 | 98:2 | 80% |
| 4 | 0.04 MgCl$_2$ | 0.5 | 1.3 | 3 h | 1% | 96% | 84:16 | 99:1 | 88% |
| 5 | 0.1 [EMIM]Cl[c] | 0.5 | 1.8 | 44 h | 3% | 85% | 78:22 | 92:8 | n.d.[g] |
| 6 | 0.1 ScCl$_3$ | 0.5 | 1.8 | 10 h | | 99% | 84:16 | 94:6 | quant.[e] |
| 7 | 0.1 CeCl$_3$ | 0.5 | 1.8 | 24 h | 3% | 94% | 84:16 | 99:1 | quant.[e] |

Decarboxylation of conjugated malonate 3b (R = Et) in the presence of boric acid and group I, II or III MX$_n$ catalysts (x = 1-3, M = group I, II or III metal, X = halide) in NMP at 160-165° C. under water-free conditions:
[a]w/w = weight equiv
[b]GC-conversions. Sub = substrate.
[c][EMIM]Cl = 1-ethyl-3-methyl-imidazolium chloride.
[d]chemical yield after aqueous work-up and distillation.
[e]crude.
[f]equiv = molar equivalents.
[g]n.d. = not determined.
[h]Conjugated malonate 3 (R = Me), 130° C., 4 w/w NMP

EXAMPLE 6

Preparation of (E)-ethyl 4-methyl-6-(2,6,6-trimethyl-cyclohex-1-enyl)hex-3-enoate 1a-Et (ethyl ester of 1a) in the presence of metaboric acid (HBO$_2$)

According to the procedure of example 4, conjugated diethyl malonate 3b (10 g, 28 mmol), anhydrous lithium chloride (0.12 g, 2.8 mol) and metaboric acid 99% (1.25 g, 28 mmol) in water-free N-methyl-pyrrolidone (19 g, 0.19 mol) gave after 23 h at 160° C., standard work-up and bulb-to-bulb distillation 6.6 g (84%) of 1a-Et (93% purity, E/Z 82:18). The analytical data of this compound are identical with the ones described for the isomers by M. Matsui et al. *Agric. Biol. Chem.* 50, 1475-1480, 1986.

The invention claimed is:

1. A process for the preparation of β,γ-unsaturated-γ,γ-disubstituted esters 1,

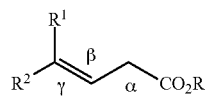

said process comprising the step of reacting at a temperature of between about 100 and 350 degrees centigrade the conjugated malonate

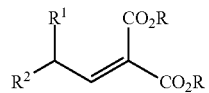

with a $MX_n$ in the presence of an inorganic proton source and optionally a polar solvent, wherein $MX_n$ is an inorganic salt or an organic cation/halide anion pair, X is a halide and n is an integer of 1 to 3, and M is a group I, II or III metal when $MX_n$ is an inorganic salt, or M is selected from the group consisting of pyrridinium, piperidinium, pyrrolidinium, imidazolium, ammonium, phosphonium and sulphonium, when $MX_n$ is an organic cation/halide anion pair; and wherein the groups $R^1$, $R^2$ and R are organic residues independently selected from the group consisting of hydrogen; and linear, branched or (poly)cyclic $C_{1-15}$ alkyl, aryl or arylalkyl groups, which optionally contain unsaturated bonds and/or 1 to 4 heteroatoms independently selected from O, S, N and Si.

2. A process according to claim 1 wherein R is methyl or ethyl.

3. A process according to claim 1 wherein $R^1$ and $R^2$ are independently selected from the group consisting of methyl, phenyl, 2-(2,6,6-trimethylcyclohex-1-enyl)-ethyl, and 4,8-dimethylnona-3,7-dien-1-yl.

4. A process according to claim 1 wherein $R^1$ is methyl, ethyl or phenyl and $R^2$ is 2-(2,6,6-trimethylcyclohex-1-enyl)-ethyl or 4,8-dimethylnona-3,7-dien-1-yl.

5. A process according to claim 1 wherein the double bond of ester 1 is in the β-γ position.

6. A process according to claim 5 wherein $R^1$ is methyl or ethyl and $R^2$ is 2-(2,6,6-trimethylcyclohex-1-enyl)-ethyl or 4,8-dimethylnona-3,7-dien-1-yl.

7. A process according to claim 1 wherein $MX_n$ is selected from the group consisting of a lanthanide halide, an alkali or alkaline earth halide and mixtures thereof.

8. A process according to claim 7 wherein $MX_n$ is selected from LiCl or $MgCl_2$, or a mixture thereof.

9. A process according to claim 1 wherein the polar solvent is an N-substituted pyrrolidone.

10. A process according to claim 1 wherein the inorganic proton source is a proton source having a $pK_a$ of about 0 to about 17.

11. A process according to claim 10 wherein the inorganic proton source is selected from the group consisting of water; boric acid; a boric acid proton donor selected from metaboric acid ($HBO_2$), monoalkyl or monoaryl boric esters ($ROB(OH)_2$ with R=alkyl, aryl or substituted analogs thereof, bisalkyl or bisaryl boric esters ($HOB(OR)_2$ with R=alkyl, aryl or substituted analogs thereof, alkylidene, arylidene or arylalkylidene bridged borates, whose bridges can carry a substituent; sodium hydrogen phosphate; and mixtures thereof.

12. A process according to claim 1 wherein the inorganic proton source is boric acid; the polar solvent is an N-substituted pyrrolidone and $MX_n$ is LiCl or $MgCl_2$.

13. A process of preparing (3aR,5aS,9aS,9bR)-3a,6,6,9a-tetramethyl-dodecahydro-naphtho[2,1-b]furan, according to the process defined in claim 1.

14. A process according to claim 11 wherein the bridge substituent is a linker to other borate units.

* * * * *